(12) United States Patent
Brogioli et al.

(10) Patent No.: US 7,268,874 B2
(45) Date of Patent: Sep. 11, 2007

(54) METHOD OF MEASURING PROPERTIES OF DISPERSED PARTICLES IN A CONTAINER AND CORRESPONDING APPARATUS

(75) Inventors: Doriano Brogioli, Milan (IT); Marzio Giglio, Milan (IT); Alberto Vailati, Milan (IT); Marco Potenza, Milan (IT)

(73) Assignee: INFM Istituto Nazionale per La Fisica Della Materia, Genoa (IT)

( * ) Notice: Subject to any disclaimer, the term of this patent is extended or adjusted under 35 U.S.C. 154(b) by 379 days.

(21) Appl. No.: 10/480,997

(22) PCT Filed: Jun. 17, 2002

(86) PCT No.: PCT/IT02/00396

§ 371 (c)(1),
(2), (4) Date: Jul. 6, 2004

(87) PCT Pub. No.: WO02/103332

PCT Pub. Date: Dec. 27, 2002

(65) Prior Publication Data

US 2004/0239932 A1      Dec. 2, 2004

(30) Foreign Application Priority Data

Jun. 18, 2001   (IT) .............................. TO01A0588

(51) Int. Cl.
*G01N 21/00*   (2006.01)
*G01N 15/02*   (2006.01)

(52) U.S. Cl. ...................... 356/336; 356/434
(58) Field of Classification Search ........ 356/335–343, 356/27–28, 28.5; 250/574–575, 222.2, 227.11
See application file for complete search history.

(56) References Cited

U.S. PATENT DOCUMENTS

| | | | | |
|---|---|---|---|---|
| 3,520,610 A | | 7/1970 | Parrent et al. | |
| 3,706,495 A | * | 12/1972 | Dotson, Jr. | ................... 356/28 |
| 5,296,910 A | * | 3/1994 | Cole | .......................... 356/28.5 |
| 5,793,478 A | * | 8/1998 | Rader et al. | ................... 356/28 |
| 5,818,583 A | * | 10/1998 | Sevick-Muraca et al. | ... 356/336 |
| 5,905,568 A | | 5/1999 | McDowell et al. | |
| 6,091,492 A | | 7/2000 | Strickland et al. | |
| 6,219,138 B1 | * | 4/2001 | Swanson et al. | ............ 356/336 |
| 6,809,820 B2 | * | 10/2004 | Snelling et al. | ............. 356/337 |

FOREIGN PATENT DOCUMENTS

EP      0 641 542 A2     3/1995

OTHER PUBLICATIONS

M. Giglio, et al.: "Space Intensity Correlations in the Newar Field of the Scattered Light: A Direct Measurement of the Density Correlation Function g(r)" Physical Review Letter, vol. 85, No. 7, Dec. 23, 1999-Aug. 14, 2000, pp. 1416-1419, XP002225445.

* cited by examiner

*Primary Examiner*—Sang H. Nguyen
(74) *Attorney, Agent, or Firm*—Sughrue Mion, PLLC

(57) ABSTRACT

A method of measuring properties of particles immersed in a body (B), comprising the performing of a series of instantaneous acquisitions by illumination of the body with a temporally coherent light beam (152) of predetermined width D and predetermined wavelength λ such as to generate scattered radiation (155) by scattering interaction of the light beam with the particles, and the detection of a plurality of values of the intensity of the total radiation (155, 156 155',156') coming from the body at a plurality of points simultaneously, the points being at a distance z from the body such that the points can receive the scattered radiation (155, 155') which comes from substantially all of the directions in which the particles are capable of scattering, and that each of the points receives the scattered radiation (155, 155') of a large number of particles, and processing (100) of the series of acquisitions in a manner such as to determine the properties of the particles.

19 Claims, 4 Drawing Sheets

US 7,268,874 B2

METHOD OF MEASURING PROPERTIES OF DISPERSED PARTICLES IN A CONTAINER AND CORRESPONDING APPARATUS

This is a National Stage Entry of Application No. PCT/IT02/00396 filed June 17, 2002; the disclosure of which is incorporated herein by reference.

BACKGROUND OF THE INVENTION

The present invention relates to a method of analyzing properties of particles immersed in a body and, in particular, to a method of determining the dimensions of particles immersed in a transparent body and to the corresponding apparatus.

A particular and advantageous application of the present invention consists in the measurement of diameter distribution in particulate material, for example, in powders, vapours, cements, pharmaceutical products, or of particles in transparent colloidal suspensions, for example, in paints, glues, or creams.

The method and the apparatus according to the present invention are based on the following physical principle: each particle struck by an incident electromagnetic field generates a spherical wave, defined as a spherical scattering wave, with an amplitude which varies angularly according to the so-called form factor which is associated with the particle, and is dependent on the size of the particle. Typically, most of the power scattered by a single particle falls within a solid angle the linear aperture of which is of the order of the ratio between the wavelength of the radiation and the size of the particle. At a certain moment, the radiation scattered by all of the particles immersed in a body is the result of the sum of the waves generated by the individual particles. This gives rise to stochastic interference phenomena which generate, on a plane placed at a predetermined distance, an arrangement of small irregular dots or fluctuations in the intensity of the scattered radiation, which are known in the art as speckles.

Conventional techniques for measuring properties of particles which use the principles described briefly above, enable the intensity of the light scattered a long distance from the sample to be measured. This intensity is substantially a mean intensity with respect to the above-mentioned fluctuations upon variation of a detection angle. In a conventional instrument, it is consequently necessary to have sensors which can move between different angular positions, or special multi-element sensors which can simultaneously detect this intensity, averaged over the speckles, in a plurality of angular positions. In any case, a delicate system of optical alignment components is always required for the correct operation of the apparatus. Conventional instruments are consequently somewhat complex and bulky, with quite expensive mechanical and optical parts.

In the document Physical Review Letters, Vol. 85, No. 7, 14 August 2000, two of the authors of which are designated inventors of the present invention, an apparatus is described which comprises a source of a wide laser beam, and a CCD sensor which detects substantially solely the radiation of the laser beam which is scattered by a body subjected to measurement, placed a short distance from the sensor such that the following equations are true:

$$z < \frac{dD}{\lambda} \quad (1)$$

and $$z > \frac{d^2}{\lambda} \quad (2)$$

where $\lambda$ is the wavelength of the laser beam, z is the distance of the sensor from the body, D is the diameter of the laser beam, and d is a characteristic size of the particles contained in the body, for example, the mean diameter. In this condition, even though the body is illuminated over an area equal to the cross-section of the laser beam, the radiation scattered is propagated in a manner such that each sensitive element of the CCD, or pixel, receives substantially solely radiation scattered by the points of the body in the directions included in a solid angle which has its vertex at the pixel, and which is equal to the solid angle in which the scattered radiation is emitted. A consequence of this phenomenon is that the diameter of the speckles is equal to the diameter of the particles and the value of this diameter does not depend on the distance of the sensor from the body, provided that equations (1) and (2) remain valid.

The instrumental apparatus described in the above-mentioned documents also comprises a lens interposed between the body and the sensor and a metal wire which is extended in the focal plane of the lens, between the lens and the sensor and extending through the focus of the lens. The lens is capable of magnifying the dimensions of the speckles on the sensor so that each speckle covers a plurality of pixels. Moreover, the lens cooperates with the metal wire in a manner such as to focus on the wire the portion of the incident field which is transmitted through the sample, and to deflect the transmitted portion so that it does not reach the sensor.

The CCD sensor simultaneously detects a plurality of values of the intensity of the scattered radiation, one for each of the sensitive elements, and provides corresponding signals to a processing unit. This plurality of values of the intensity of the scattered radiation corresponds to the configuration of speckles detected by the CCD sensor.

An example of the measurement method performed by this apparatus is illustrated in FIG. 1.

In order for processing 100 of these signals to achieve an accurate evaluation of the particle dimensions, it is necessary to perform a series of consecutive instantaneous acquisitions, for example, a number N of acquisitions of the intensity, detected by the CCD sensor, of the radiation scattered by the same body.

As will be appreciated, the processing 100 of the signals comprises, initially, a determination of a plurality of spatial correlation functions of the intensity 110 which correspond to the plurality of scattered radiation intensity values detected in the series of acquisitions. This operation comprises a calculation, for each pixel, of the mean intensity 111 of the intensity values obtained in the series of acquisitions in the same pixel, a calculation of the mean 112 of the mean intensity values obtained in all of the pixels, a calculation of a plurality of spatial correlation functions of the intensity 113, one for each acquisition, and a calculation of a spatial correlation function of the said mean intensity 114. The calculation of the correlation functions may be performed by known methods such as the fast Fourier transform, correcting the result taking into account the finite dimensions of the image. In the drawings, $I_n(\vec{x})$ is the scattered radiation intensity value detected in the pixel of coordinate $\vec{x}$ in the nth acquisition, $\bar{I}(\vec{x})$ is the mean intensity of the intensity values obtained in the series of acquisitions for each pixel, $\bar{\bar{I}}$ is the mean of all of the mean intensity values $\bar{I}(\vec{x})$ with respect to $\vec{x}$, $C_n(\Delta \vec{x})$ is a spatial correlation function of the intensity between two pixels having a vectorial distance $\Delta \vec{x}$ from one another, relating to the nth acquisition, and $C_0(\Delta \vec{x})$ is a spatial correlation function of the mean intensity $\bar{I}(\vec{x})$.

The processing 100 of the signals then comprises a derivation of an electric-field spatial correlation function 120 from the plurality of intensity spatial correlation functions. This operation comprises a calculation of the mean of the intensity spatial correlation functions 121 relating to the series of acquisitions and a calculation of a correlation function of the electric field 122. The calculation 122 is performed with the use of the so-called Siegert equation which relates the intensity correlation function to the electric-field correlation function. It is consequently possible to calculate the electric-field correlation function in relation to the other quantities previously calculated. In the drawings, $\overline{C}(\Delta \vec{x})$ is the mean of the intensity spatial correlation functions and $c(\Delta \vec{x})$ is the electric-field correlation function.

Finally, the processing 100 of the signals comprises a determination of a power spectrum of the electric field 130 corresponding to the electric-field correlation function. This operation comprises a calculation of a spectrum of the electric-field correlation function 131 by the fast Fourier transform and a calculation of the mean of that spectrum 132 over the values of the transferred wave vector which have the same modulus so as to obtain a power spectrum of the electric field. In the drawings, $S(\vec{q})$ is the power spectrum of the electric field as a function of the transferred wave vector $\vec{q}$, and $S(q)$ is the power spectrum of the electric field as a function of the modulus of the transferred wave vector q.

The electric-field spectrum thus obtained enables the distribution of the dimensions of the particles to be determined by known methods normally used in conventional techniques for the measurement of particle dimensions by measurement of scattered light, which methods will not therefore be described herein.

The method described above may require a large number of acquisitions to be performed in order to be able to eliminate the noise which inevitably afflicts the measurement and thus to obtain an adequate determination of the properties of the particles. Moreover, to be able to calculate the correlation functions of the field on the basis of the intensity correlation functions, it is necessary for the scattered radiation to be capable of being described as a random Gaussian process. Furthermore, although the apparatus is of simple construction, it nevertheless requires correct positioning of the reflecting wire at the focus of the lens.

SUMMARY OF THE INVENTION

The object of the present invention is to provide a method and apparatus which do not require complex optical configurations and which permit a statistical analysis which is more accurate than that already described and which is particularly suitable for the purposes of the determination of particle-diameter distribution.

This object is achieved, according to the invention, by a method of analyzing properties of particles immersed in a body and by corresponding apparatus which have the characteristics defined in the claims.

Advantageously, with a particular embodiment of the invention, it is possible also to implement an analysis method which does not depend on accurate positioning of the components of the apparatus.

A preferred but non-limiting embodiment of the invention will now be described with reference to the appended drawings, in which:

DETAILED DESCRIPTION OF THE INVENTION

Figure 2:
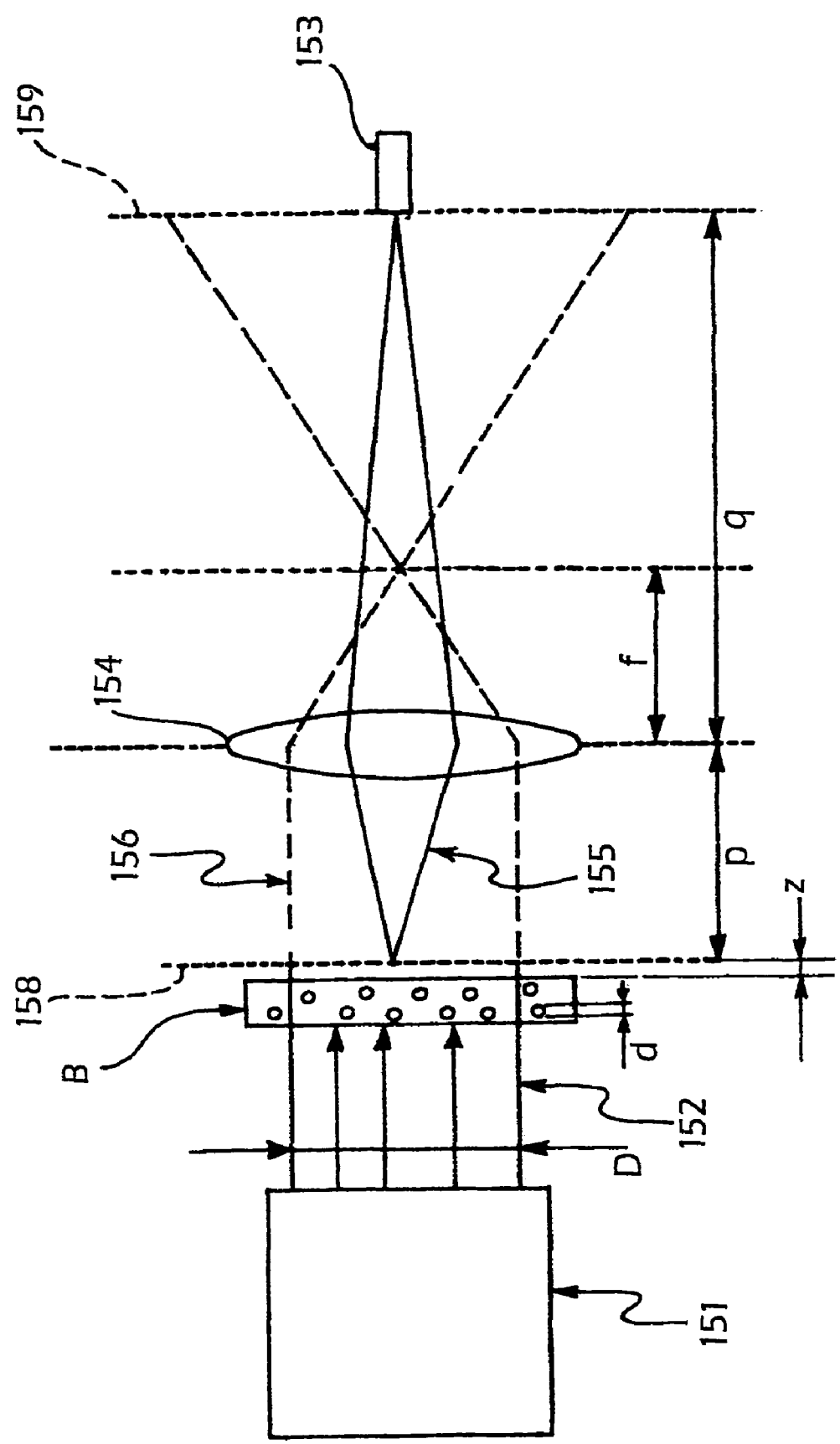
FIG. 2 is a schematic view of apparatus for implementing a measurement method according to the invention.

FIG. 2 shows schematically apparatus for implementing a measurement method in accordance with the invention. The apparatus comprises a source 151 of a laser beam 152 having a predetermined wavelength λ and a predetermined width D. The source 151 is composed of a generator of temporally coherent light, preferably a laser, for example, a He—Ne or semiconductor laser which emits in the visible spectrum, a spatial filter, and a collimator lens (not shown). The parallel arrows emerging from the source 151 indicate the direction of propagation of the laser beam 152.

Sensor means 153 which are capable of detecting a plurality of values of the intensity of an electromagnetic radiation at a plurality of points simultaneously are aligned along the main axis of propagation of the laser beam. Preferably, the sensor means are configured in a manner such as to form a rectangular matrix of a plurality of sensitive elements each of which is capable of detecting a value of the intensity of the electromagnetic radiation at a distinct point. Even more preferably, the sensor means 153 comprise a CCD sensor.

A body B subjected to measurement is located at a position interposed between the source 151 and the sensor means 153 and aligned therewith. The body is generally made of a material which is transparent to the laser beam 152, and immersed in which are particles having a predetermined distribution of dimensions, a characteristic size, for example, the mean diameter, being generally indicated d. If the transparent material in which the particles are immersed is fluid, the body B is contained in a suitable container which is transparent to the laser beam 152. The particles may be composed of any material and, in order to be measurable, must have dimensions greater than or equal to the wavelength λ.

The sensor means 153 are disposed substantially at a distance z from the body B such that equation (1) is valid, so that the sensor means 153 receive the scattering radiation which comes from all of the directions in which the particles are substantially capable of scattering. Equation (2) must also be valid so that each sensitive element receives the radiation scattered by a large number of particles, to permit the processing of the data by statistical analysis of the measurements which will be described further below. More precisely, the number of particles scattered towards each sensitive element must be sufficient to fall within Gaussian statistics. For example, this number may be a few tens of particles.

The laser beam 152 interacts with the particles of the body B, giving rise to scattered radiation 155. A transmitted portion 156 of the laser beam 152, indicated by broken lines, also passes through the body B but does not interact with the particles. The transmitted portion 156 and the scattered radiation 155 are mixed and interfere with one another. The sensor 153 is thus capable of detecting a plurality of values of the intensity of the total radiation coming from the body in a plurality of sensitive elements simultaneously. That is, the transmitted portion 156 and the scattered radiation 155 form, by interference, on the sensor 153, substantially a speckled image corresponding to the plurality of different intensity values detected in the plurality of sensitive elements.

If the particles included in the sample B are very small, speckles smaller than each individual sensitive element may be generated on the sensor means 153, which does not allow useful measurements to be made.

Magnifying lens means 154 are therefore preferably interposed between the body B and the sensor means 153 so as to obtain magnified images of the speckles on the sensor 153. With this configuration, the distance z which appears in equations (1) and (2) is the distance from the body B of a plane 158, close to the body B which is conjugated with an image plane 159 by means of the lens 154. The detection of the plurality of intensity values thus takes place indirectly by detection of the corresponding values in the image plane 159 optically conjugated with the plane 158. The image plane 159 is defined by the position of the sensor means 153. The lens means 154 are disposed substantially at a distance p from the plane 158 and at a distance q from the sensor 153 (and hence from the image plane 159), which is considerably greater than a focal distance f of the lens means 154. The image which would be formed in the plane 158 is thus magnified on the sensor 153 by a factor equal to the ratio between q and p. As will be appreciated from the following, an image formed on the sensor 153 is not a focused image of the body B but an image of the plane 158 at a distance z from the body B. It is important that the angles at which the radiation 155 is scattered be reproduced on the sensor 153 by the lens means 154 in accordance with a known law, without distortions or limitations. Moreover, the lens means 154 must have a numerical aperture sufficient for resolution of the dimensions of the smallest particles to be analyzed. The lens means 154 may thus comprise, for example, a suitable microscope objective.

The sensor 153 also supplies to a processing unit (not shown) signals corresponding to the plurality of detected values of the intensity of the total radiation coming from the body, typically a matrix of data.

Figure 3:
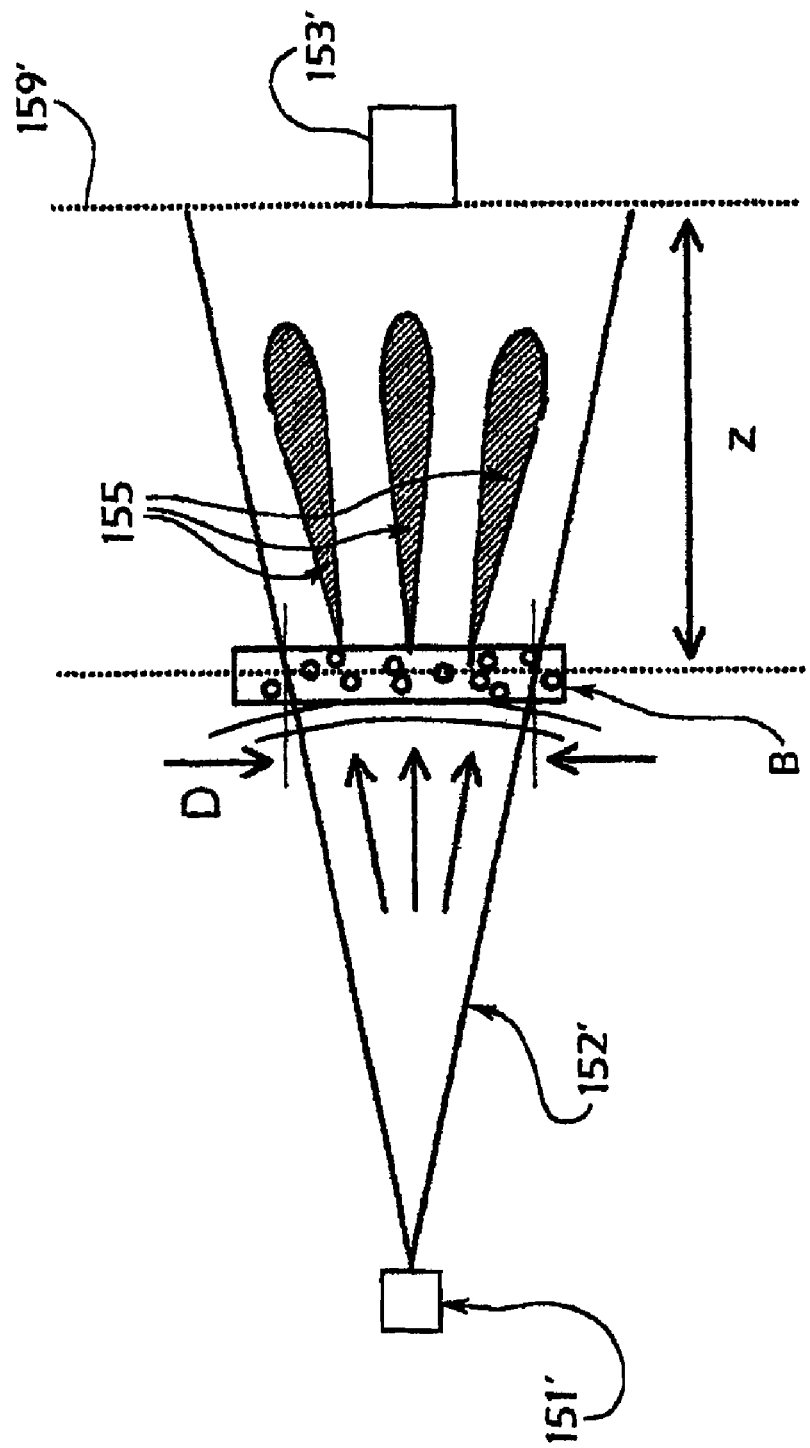
FIG. 3 is a schematic view of a second embodiment of the apparatus according to the invention.

A second embodiment is shown in FIG. 3 which shows, by way of example, a schematic view of apparatus similar to the apparatus described above for implementing a measurement method according to the invention.

A light source 151' comprises a generator of temporally coherent light which sends the light to shaping optics of known type (not shown) so as to produce a wavefront which is not plane (for example, a diverging front). The diverging arrows emerging from the source 151' indicate the direction of propagation of the light beam 152'. As in the previous embodiment, the light beam 152', which has a predetermined width D in the region of the body B and a predetermined wavelength $\lambda$, falls on the body B subject to measurement and thus interacts with the bodies contained therein, a portion of the beam giving rise to scattered radiation 155' and a portion continuing undisturbed as a transmitted portion 156' (indicated by broken lines).

Sensor means 153', identical to those described above, are disposed substantially at a distance z from the body B such that the said means receive the scattered radiation 155' which comes from all of the directions in which the particles are substantially capable of scattering, and that each sensitive element receives the radiation scattered by a large number of particles. In order for this to occur, the distance z must be such that near field equations similar to equations (1) and (2), but which are valid in the more general case in which the light beam (152') has a curved wave front, are true. The generalization of equations (1) and (2) for a beam with a curved wave front can be achieved in a manner known to a person skilled in the art and will not therefore be described herein.

The scattered radiation 155' and the transmitted portion 156' mix together, interfering with one another and forming a speckled image on the sensor 153'. The dimensions of the speckles on the sensor 153' depend on the curvature of the wave front introduced by the optics for shaping the beam and on the distance z between the illuminated body B and the sensor 153', which advantageously enables magnified images of the speckles to be obtained without necessarily using the magnifying lens means 154 described above.

In an embodiment not shown, the magnifying lens means 154 may nevertheless be used in a manner similar to that described with reference to the embodiment of FIG. 2, enabling the surface of the sensor (the image plane 159') to be conjugated with a plane at a distance z from the body B, in which the detection of the plurality of intensity values takes place indirectly by detection of the corresponding values in the image plane 159'. It is important that the angles at which the radiation is scattered be reproduced on the sensor 159' by the lens means 154 without distortions or limitations, in accordance with a known law dependent on the curvature induced in the wave front by the shaping optics. Moreover, the lens means 154 must have a numerical aperture sufficient for resolution of the dimensions of the speckles detected in the plane 159' in which the intensity is recorded. The lens means 154 may thus comprise, for example, a suitable microscope objective.

The near field conditions which are expressed mathematically by equations (1) and (2) in the case of the plane beam, and which can be generalized appropriately for a converging or diverging beam, lead to the correct formation of near field speckles. However, what is expressed by condition (2) is valid upon the approximation that the body B struck by the light is suitably thin. If the bodies contained in the body B were to become suitably small, the minimum distance expressed by (2) would thus become so small as to be comparable with the thickness of the body B. In this situation, it is fundamental to consider this thickness and the requirement expressed by condition (2) can then be satisfied by a suitable selection for the thickness of the body B. This thickness acts in a manner similar to the distance z between the body B and the sensor 153 or 153' (or, if a magnifying lens device is used, the plane 158 conjugate with the image plane 159 or 159' defined by the plurality of sensors), enabling near field speckles to be obtained even at a distance less than that expressed in (2).

In contrast with what occurs if the body B is thin relative to the distances which characterize the components of the instrument, when the body is sufficiently thick, the near field regime is also maintained at distances less than that expressed by (2) (or variations thereof which take account of the curvature of the beam). In this case, the phenomenon which causes the near field regime to fail is not present.

Figure 1:
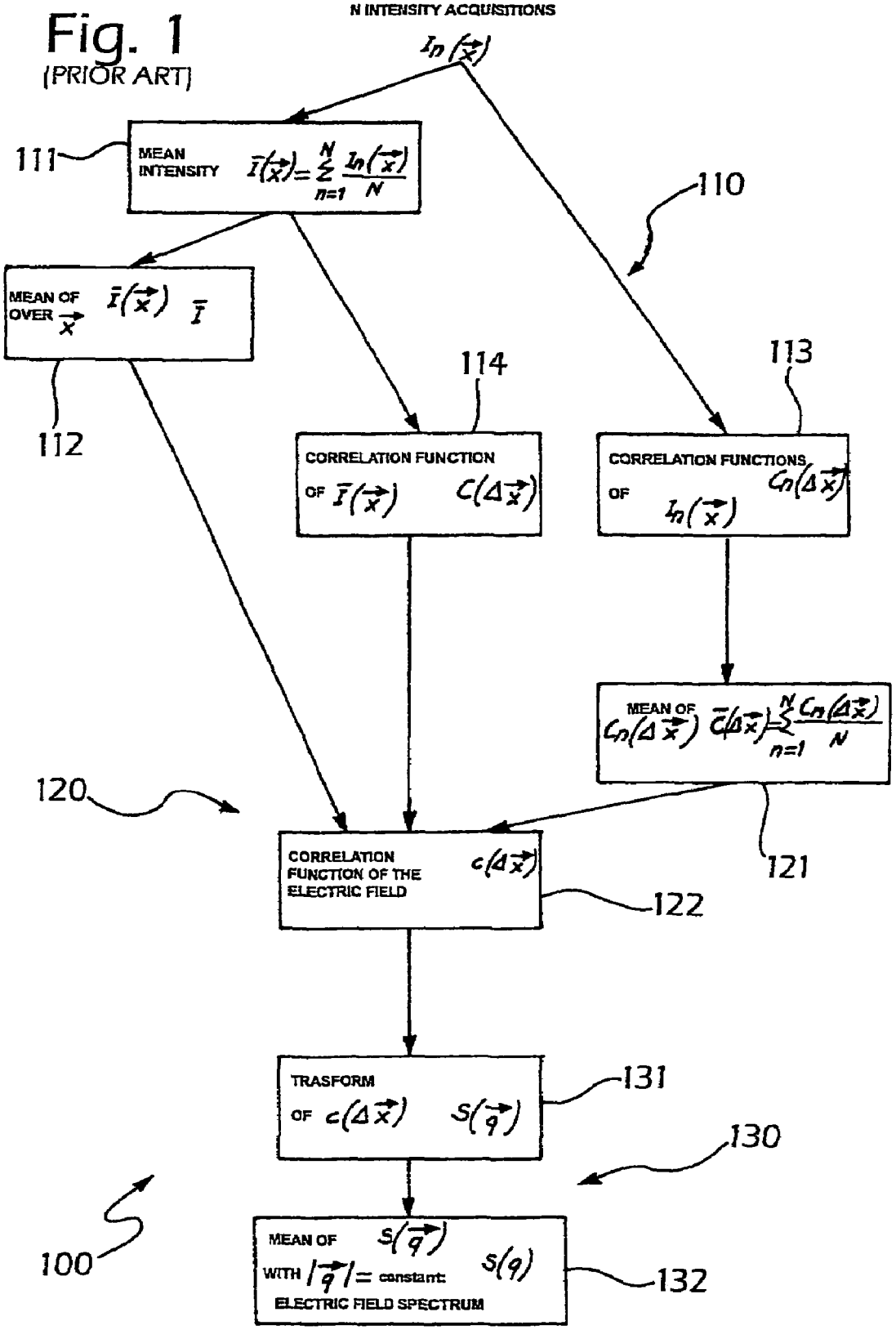
FIG. 1 is a block diagram which illustrates a measurement method according to the prior art.
Figure 4:
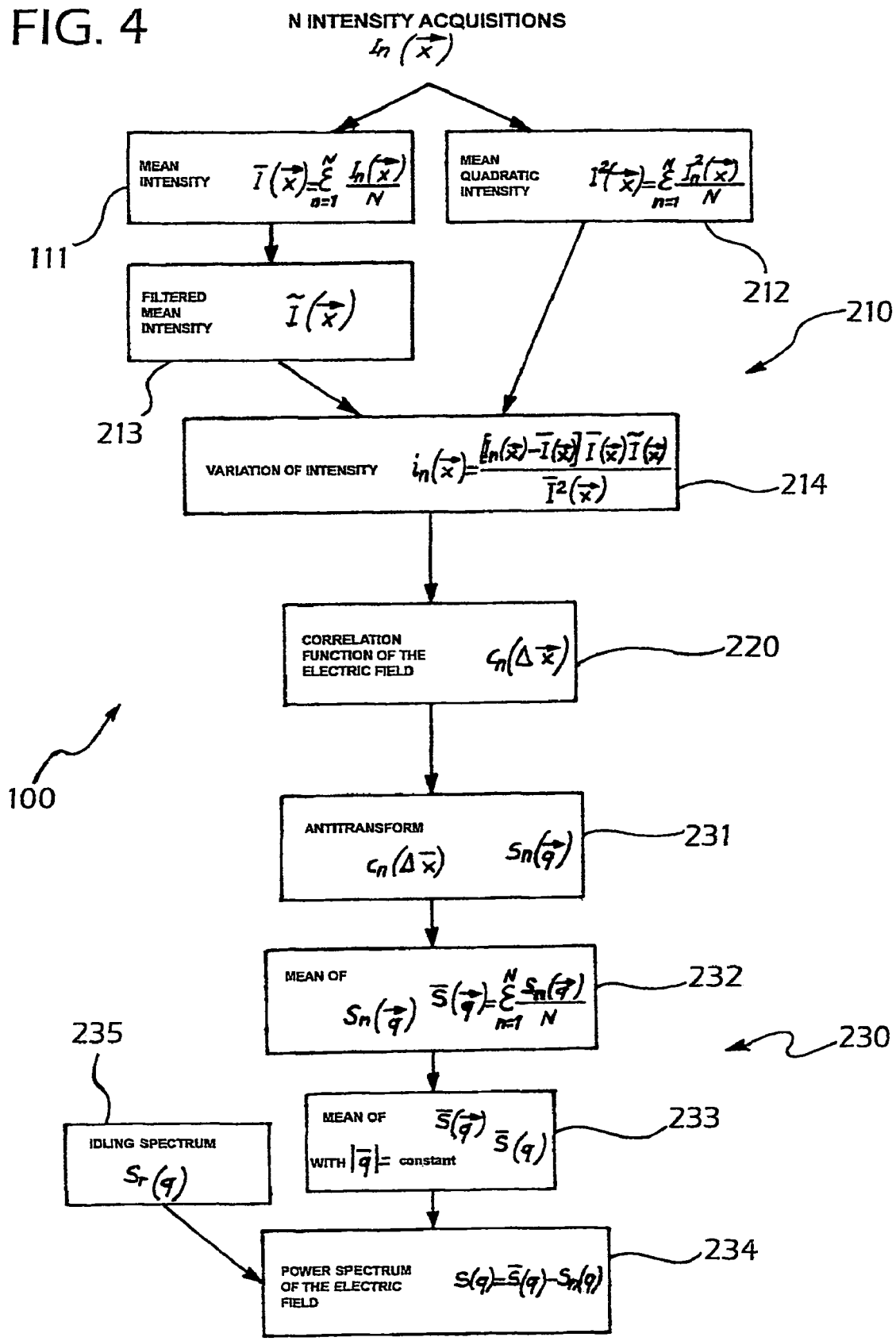
FIG. 4 is a block diagram which illustrates a measurement method according to the present invention.

A first embodiment of the measurement method according to the present invention is illustrated in FIG. 4 in which, for greater clarity, steps identical or similar to those of FIG. 1 are indicated by the same reference numerals.

In order for statistical processing 100 of the above-mentioned signals to achieve an accurate evaluation of the particle dimensions, it may be necessary to perform a series of consecutive instantaneous acquisitions, for example, a number N of acquisitions of the intensity, detected by the sensor means 153, of the total radiation coming from the same body.

If the particles contained in the body B are moving, each acquisition must be performed within a period of time which is short in comparison with the time in which the speckled image changes, and hence short in comparison with the time in which the arrangement of the particles in the body B changes.

The statistical processing 100 of the signals comprises, initially, a determination of a plurality of values substantially of a variation of intensity 210, which values correspond to the plurality of radiation intensity values detected in this series of acquisitions. This determination 210 comprises a calculation, for each sensor element, of a mean intensity 111 of the intensity values obtained in the series of measurements in the same sensor element, a calculation, for each sensor element, of a mean quadratic intensity 212 obtained from the mean of the squares of the values obtained in the series of measurements in the same sensor element, a filtering 213 by means of a low-pass spatial filter, and a calculation substantially of a variation of intensity 214 in accordance with the following equation:

$$i_n(\vec{x}) = \frac{[I_n(\vec{x}) - \bar{I}(\vec{x})]\bar{I}(\vec{x})\bar{I}(\vec{x})}{\bar{I}^2(\vec{x})} \quad (3)$$

in which $i_n(\vec{x})$ is a quantity similar to a variation of the intensity, relating to the nth acquisition, $\bar{I}(\vec{x})$ is the intensity obtained by filtering the mean intensity $\bar{I}(\vec{x})$, and $\bar{I}^2(\vec{x})$ is the above-mentioned mean quadratic intensity.

The statistical processing 100 of the signals then comprises a determination of a plurality of spatial correlation functions of the electric field 220, corresponding to the plurality of values of substantially the variation of intensity. This operation comprises a calculation of the spatial correlation function of the electric field relating to each acquisition by fast Fourier transform of the signal, taking account of the finite dimensions of the image. In the drawings, $c_n(\Delta \vec{x})$ is the correlation function of the electric field relating to the nth acquisition.

Finally, the statistical processing 100 of the signals comprises a determination of a power spectrum of the electric field 230 corresponding to the plurality of correlation functions of the electric field. This operation comprises an anti-transformation 231 of the correlation function to obtain a spectrum relating to each acquisition, a calculation of the mean of the spectra 232 over all of the acquisitions, a calculation of the mean 233 of the function thus obtained over all of the values of the transferred wave vector which have the same modulus, and the subtraction of an idling spectrum 235 from that mean so as to obtain the power spectrum of the electric field 234. The idling spectrum 235 is determined by following the method described up to now but without positioning a body B so as to interact with the laser beam 2. The effect of the electronic noise of the apparatus can thus be subtracted from the measurement. In the drawings, $S_n(\vec{q})$ is the spectrum of the signal $i_n(\vec{x})$, $\bar{S}(\vec{q})$ is the mean of the spectra $S_n(\vec{q})$ over all of the acquisitions, $\bar{S}(q)$ is the mean of $\bar{S}(\vec{q})$ with respect to the wave vectors $\vec{q}$ having the same modulus q, and $S_r(q)$ is the idling spectrum.

Finally, the power spectrum of the electric field thus obtained enables the particle size distribution to be determined by known methods normally used in conventional techniques for the measurement of particle size by measurement of scattered light, which will not be described herein.

As a person skilled in the art will appreciate, with the method according to the invention, it is no longer necessary to screen the transmitted portion 156 of the laser beam in order to be able to measure the particle dimensions; the transmitted portion thus acts as a heterodyne reference which permits a more accurate measurement. Moreover, the method according to the invention is based on a near field scattering technique which is intrinsically quantitative.

As can be seen, the present technique, which permits a direct determination of the field correlation functions, benefits from a considerable advantage over the above-described homodyne technique which is the subject of the publication in Physical Review Letters. In fact, the contributions due to particles of different diameters are added up without giving rise to mixed contributions which are present in the homodyne technique and which are difficult to subtract.

This apparatus is also particularly suitable for the measurement of particle velocity. In fact, movement of the particles constituting the sample B leads to movement of the near field speckles with a velocity proportional to that of the particles. The velocity of the particles can thus be measured by a technique for analyzing the images of the speckle fields which can determine the velocity of the speckles.

In this application also, the heterodyne configuration is fundamental since it allows the contributions to the speckle field due to particles of different sizes to be decoupled. For example, for particles in sedimentation, this means that, as when observing the sample the particles are seen in motion with a velocity which depends on their size, the same occurs with the near field speckles which faithfully follow the behaviour of the particles which give rise to them.

The present invention is based on the movement of the near field speckles (the size of which depends not on the distance z at which they are picked up, but on the size of the bodies contained in the sample B) which movement is associated with the orderly movement of the particles in the sample B. In fact, the movement of the particles constituting the sample B brings about the movement of the speckles with a velocity which depends on the curvature of the incident beam 152'.

For near field speckles, the speckles have a size proportional to that of the scattering particles and the measurement of the velocity of the particles can be achieved by a technique for analyzing the images of the speckle fields, which technique can determine the velocity of the speckles.

A second example of a measurement method which can be used to measure particle velocity and which is based on the analysis of the correlation between pairs of instantaneous images recorded at different times will now be described by way of illustration. When two such images have been taken, the method proceeds as follows: 1) the spatial frequency spectra are obtained by Fourier transform, 2) the product of the spectra obtained is worked out, 3) the cross-correlation function of the two starting images is obtained by inverse Fourier transform, 4) since the period of time which separates the two instantaneous images is known, the velocity of the speckles is obtained in conventional manner. An alternative measurement method involves direct determination of the velocity of each individual speckle on the basis of the analysis of pairs of images.

In case of particles having a rectilinear and steady motion within flow cells, of the type usually employed in conventional particle sizing apparatuses (for example, with laser Doppler velocimetry techniques), the condition of the image of the speckles being frozen can be relaxed on the basis of the following remarks.

Owing to the motion and the finite exposure during the acquisition of a single image, the speckles appear like streaks oriented along the direction of the motion. However, the analysis performed perpendicularly to the direction of the streaks preserves the whole useful information relating to the intensity distribution of the light scattered as a function of the angle. In the present case, the analysis is thereby limited to the study of the power spectrum of the image along the direction perpendicular to the motion direction.

The study of flowing particulate is particularly interesting since it allows to obtain the measure of the velocity of the material. In fact, having measured the length of the streaks of the speckles, being the exposure time known it is possible to obtain the velocity in a simple way. Moreover, as the technique based on near field scattering allows to obtain absolute measures of scattering and thereby allows to directly infer the particulate mass per unit of volume, the said velocity measurement technique allows to determine in real time the flow rate in terms of grams of material per unit of surface per second.

Further, unlike the traditional scattering techniques and the omodyne near field scattering technique, the method according to the invention based on the heterodyne near field scattering technique allows to obtain absolute measures of scattering in a simple and direct way. This is due to the fact that the scattered light interferes with the transmitted beam and the measurement of the variance of the signal in respect of the mean value provides absolute data about the scattering cross sections. It is thereby possible infer the amount of particulate material per unit of volume.

The invention is not intended to be limited to the embodiments described and illustrated herein, which should be considered as examples of the implementation of the method of measuring properties of particles immersed in a body and of the corresponding apparatus, but may undergo modifications with regard to the shape and arrangement of parts, and to details of construction and of method.

In particular, an example of the above-described data-analysis consists in examination of the two-dimensional Fourier transform of the data matrix picked up by the CCD sensor. Data-analysis methods equivalent to those described above may however be implemented by different techniques, for example, with the use of two-dimensional cross-correlation or auto-correlation techniques, or direct determination of the velocity of each individual speckle on the basis of the analysis of several images.

Moreover, the invention is not necessarily limited to the measurement of particle dimensions but can be used for the measurement of other properties which can be deduced from the spectrum of the electric field, in accordance with any variants which may appear suitable to a person skilled in the art and which should be considered to be included within the scope of the invention as defined by the appended claims.

What is claimed is:

1. A method of measuring properties of particles immersed in a body, comprising:
   the performing of a series of instantaneous acquisitions, wherein each acquisition comprises
   a) illuminating the body with a temporally coherent light beam of predetermined width D and predetermined wavelength $\lambda$, in order to generate scattered radiation by scattering interaction of the light beam with the particles, and
   b) detecting a plurality of values of the intensity of the total radiation coming from the body at a plurality of points simultaneously, the points being substantially on a plane at distance z from the body such that the points can receive the scattered radiation which comes from substantially all of the directions in which the particles are capable of scattering, and that each of the points receives the scattered radiation of a large number of particles, whereby a near field speckled image is created on said plane, corresponding to said plurality of intensity values, wherein said detecting step provides a digital image signal indicative of said near field speckled image, and
   processing of the digital image signals of the series of acquisitions by means of image analysis in order to determine size and motion properties of the particles correlated to said near field speckled image.

2. A method according to claim 1 in which the light beam has a plane wave front and the distance z is such that the equation $$z < \frac{dD}{\lambda},$$

in which d is a characteristic size of the particles contained in the body, D is a width of the light beam and $\lambda$ is the wavelength of the light beam, is valid.

3. A method according to claim 2, in which the distance z is such that the equation $$z > \frac{d^2}{\lambda}$$

is also valid.

4. A method according to claim 1 in which the light beam has a curved wave front and the distance z is such as to satisfy near field conditions in the case of an incident light beam having a curved wave front.

5. A method according to claim 1 in which the total radiation coming from the body (B) comprises a portion which is transmitted through the body and a portion which is scattered from the body, which portions interfere with one another.

6. A method according to claim 1 in which the radiation is detected at a plurality of points belonging to a single plane.

7. A method according to claim 6 in which the detection takes place indirectly by detection of a plurality of intensity values in an image plane optically conjugated with the plane.

8. A method according to claim 7 in which the illumination and the detection are performed on opposite sides of the body.

9. A method according to claim 6, in which the processing of the series of acquisitions is programmed in a manner such as to permit determination of the distribution of the diameters of the particles immersed in the body.

10. A method according to claim 9 in which the processing comprises:
   determination of a plurality of values substantially of a variation of intensity, which values correspond to the plurality of radiation intensity values detected in the series of acquisitions, and
   determination of a power spectrum of the electric field corresponding to the plurality of values substantially of a variation of intensity.

11. A method according to claim 10 in which the determination of a power spectrum of the electric field is preceded by a determination of a plurality of spatial correlation functions of the electric field corresponding to the plurality of values substantially of a variation of intensity.

12. A method according to claim 11 in which the processing further comprises a filtering of the plurality of radiation intensity values, by means of a low-pass spatial filter prior to the determination of the plurality of values substantially of a variation of intensity.

13. A method according to claim 6 in which the processing of the series of acquisitions is programmed in a manner such as to permit the determination of the distribution of the velocities of the speckles which correspond to the plurality of radiation intensity values and which are created in the plane of detection of the total radiation coming from the body.

14. A method according to claim 13 in which the distribution of velocities of the speckles is used to determine the sedimentation rate of the particles immersed in the body.

15. A method according to claim 14 in which the processing of the series of acquisitions comprises an analysis of the correlation between the intensities relating to pairs of instantaneous acquisitions performed at different times.

16. Apparatus arranged for implementing the measurement method according to claim 1, comprising:
   a source of the light beam, suitable for the illumination of the body,
   sensor means suitable for detecting the radiation at a plurality of points simultaneously and for making available a signal indicative of the detection, and
   processing means suitable for processing the series of acquisitions by processing of the signal.

17. Apparatus according to claim 16, further comprising magnifying lens means interposed between the body and the sensor means so as to permit indirect detection by detection of the plurality of intensity values in the image plane optically conjugated with the plane, in accordance with a magnification relationship.

18. Apparatus according to claim 16 in which the sensor means comprise a CCD sensor.

19. A method according to claim 1, wherein the body is a flowing material.

* * * * *